(12) United States Patent
Hart et al.

(10) Patent No.: US 6,183,492 B1
(45) Date of Patent: Feb. 6, 2001

(54) PERFUSION-ISOLATION CATHETER APPARATUS AND METHOD

(76) Inventors: Charles C. Hart, 8252 Mandeville, Huntington Beach, CA (US) 92646; Paul D. Hansen, 2226 SE. 55th Ave., Portland, OR (US) 97215; Said Hilal, 25291 Spindlewood; Mark Ashby, 10 Bellcrest, both of Laguna Niguel, CA (US) 92677; Lee L. Swanstrom, 1405 NW. 24th Ave., Portland, OR (US) 97227; Bounsavanh Pravongviengkham, 450 Wilson Cir., Corona, CA (US) 91719; John R. Brustad, 34056 Formosa Dr., Dana Point, CA (US) 92629

( * ) Notice: Under 35 U.S.C. 154(b), the term of this patent shall be extended for 0 days.

(21) Appl. No.: 09/141,196

(22) Filed: Aug. 27, 1998

Related U.S. Application Data

(60) Provisional application No. 60/057,130, filed on Aug. 28, 1997.

(51) Int. Cl.[7] .................................................... A61M 29/00
(52) U.S. Cl. .............................. 606/194; 606/198; 604/96
(58) Field of Search ............................... 606/1, 108, 191, 606/192, 194, 195, 198; 604/96–101; 623/1.1, 1.11

(56) References Cited

U.S. PATENT DOCUMENTS

| | | |
|---|---|---|
| 1,271,456 | 7/1918 | Flack . |
| 4,183,102 | 1/1980 | Guiset . |
| 4,407,271 | 10/1983 | Schiff . |
| 4,437,856 | 3/1984 | Valli . |
| 4,535,757 | 8/1985 | Webster, Jr. . |
| 4,689,041 | 8/1987 | Corday et al. . |
| 5,000,734 | 3/1991 | Boussignac et al. . |
| 5,002,531 * | 3/1991 | Bonzel ............................. 606/194 |
| 5,041,093 | 8/1991 | Chu . |
| 5,108,370 | 4/1992 | Walinsky . |
| 5,226,887 | 7/1993 | Farr et al. . |
| 5,354,310 | 10/1994 | Garnic et al. . |
| 5,370,617 | 12/1994 | Sahota . |
| 5,378,237 | 1/1995 | Boussignac et al. . |
| 5,409,460 | 4/1995 | Krumme . |
| 5,470,314 | 11/1995 | Walinsky . |
| 5,522,800 | 6/1996 | Crocker . |
| 5,542,925 | 8/1996 | Orth . |
| 5,542,926 * | 8/1996 | Crocker ............................. 606/194 |
| 5,554,180 | 9/1996 | Turk . |
| 5,611,812 * | 3/1997 | Skornia ............................. 606/194 |
| 5,653,684 | 8/1997 | Laptewicz et al. . |
| 5,685,826 | 11/1997 | Bonutti . |
| 5,700,242 | 12/1997 | Mulder . |
| 5,749,883 | 5/1998 | Halpern . |
| 5,759,172 * | 6/1998 | Weber et al. ...................... 606/194 |
| 5,895,405 * | 4/1999 | Inderbitzen ........................ 606/194 |

* cited by examiner

*Primary Examiner*—Michael Buiz
*Assistant Examiner*—William Lewis

(57) ABSTRACT

A catheter includes an introducer and a flow isolator adapted for disposition in a primary conduit to facilitate flow in the primary conduit while inhibiting flow and intersecting secondary conduits. The flow isolator may include a tubular mesh and surrounding balloon structure. Alternatively, a sleeve can be provided with a primary opening and a secondary opening which are sized to inflate the sleeve with the body fluid. Structures for deploying the sleeve between a low-profile state and high-profile state may include expandable fingers, or pneumatic chambers inflatable from an external source. In operation the sleeve can be forced by the body fluid against the intersection with the secondary conduits to achieve isolation. Alternatively, the pneumatic chambers can be inflated to form seals with the primary conduit. A blood filter or snare is contemplated to filter any blood clots which may develop around the flow isolator.

22 Claims, 18 Drawing Sheets

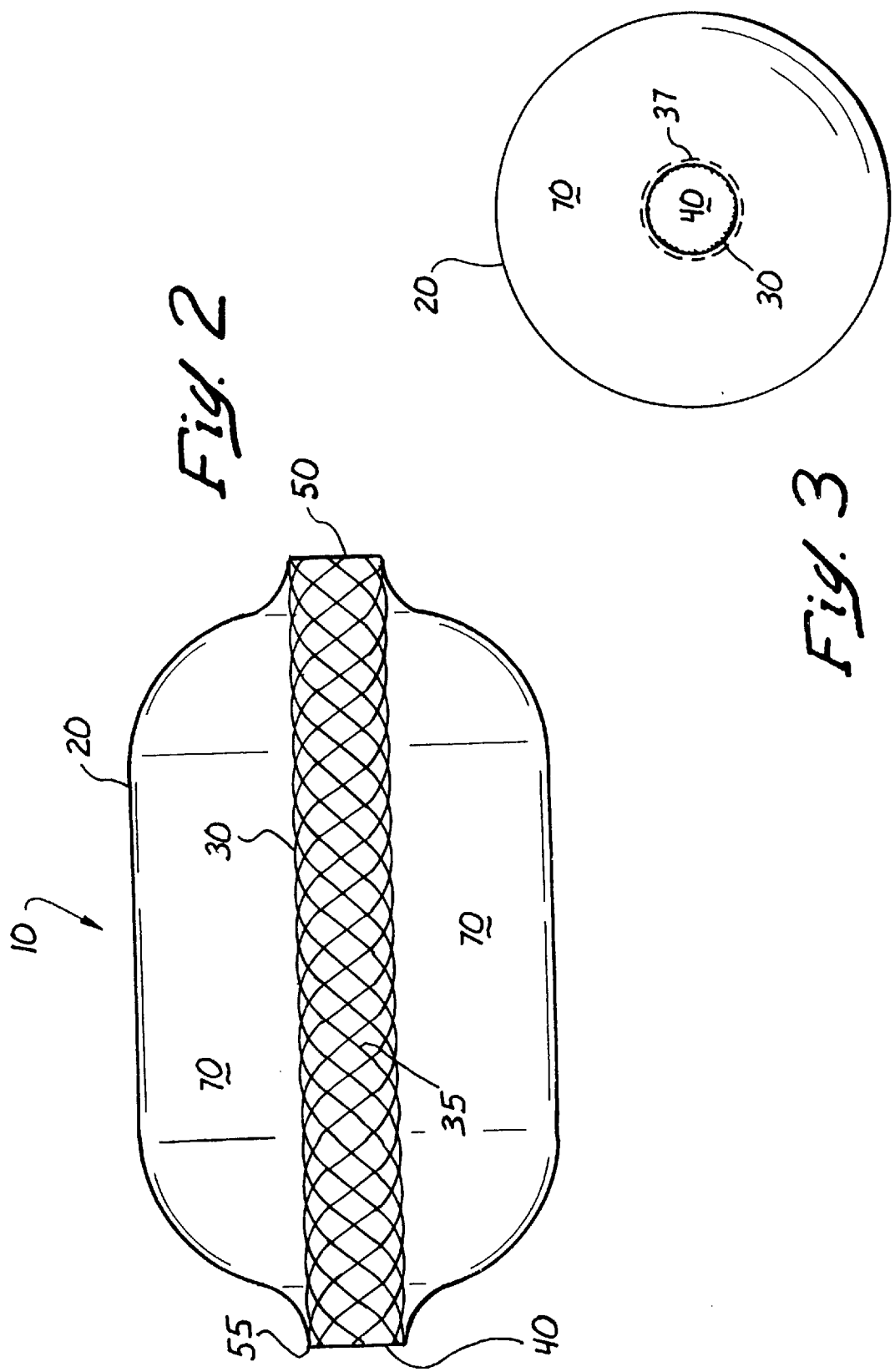

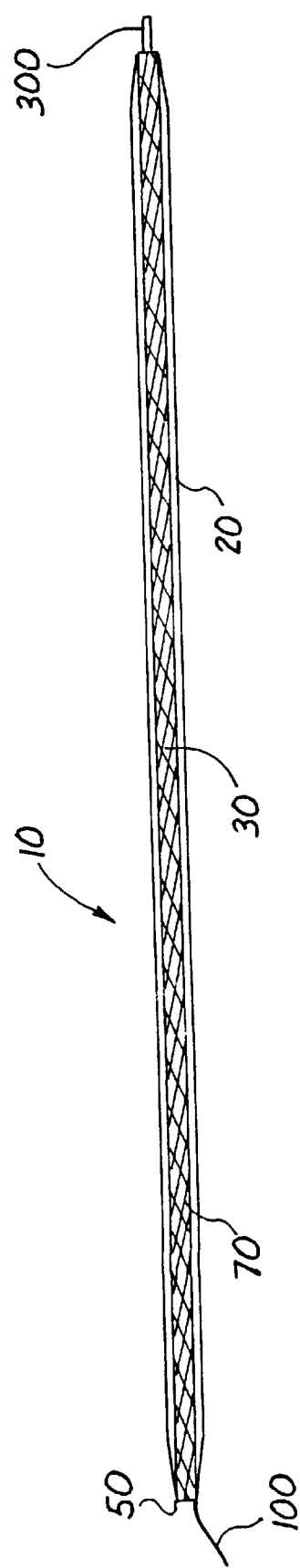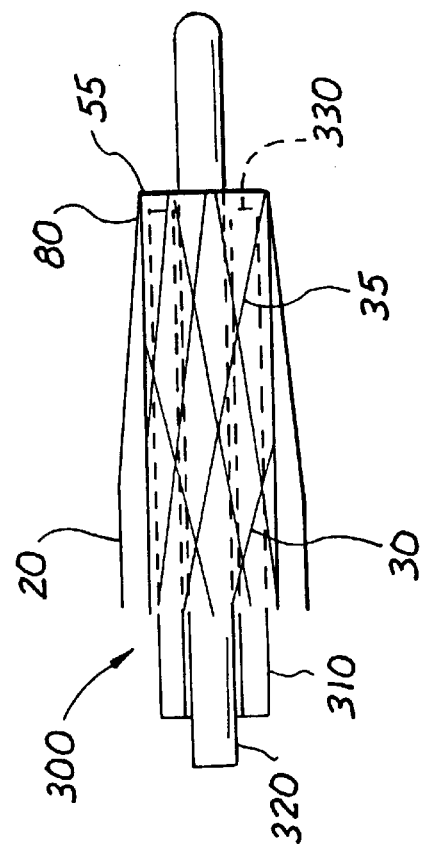

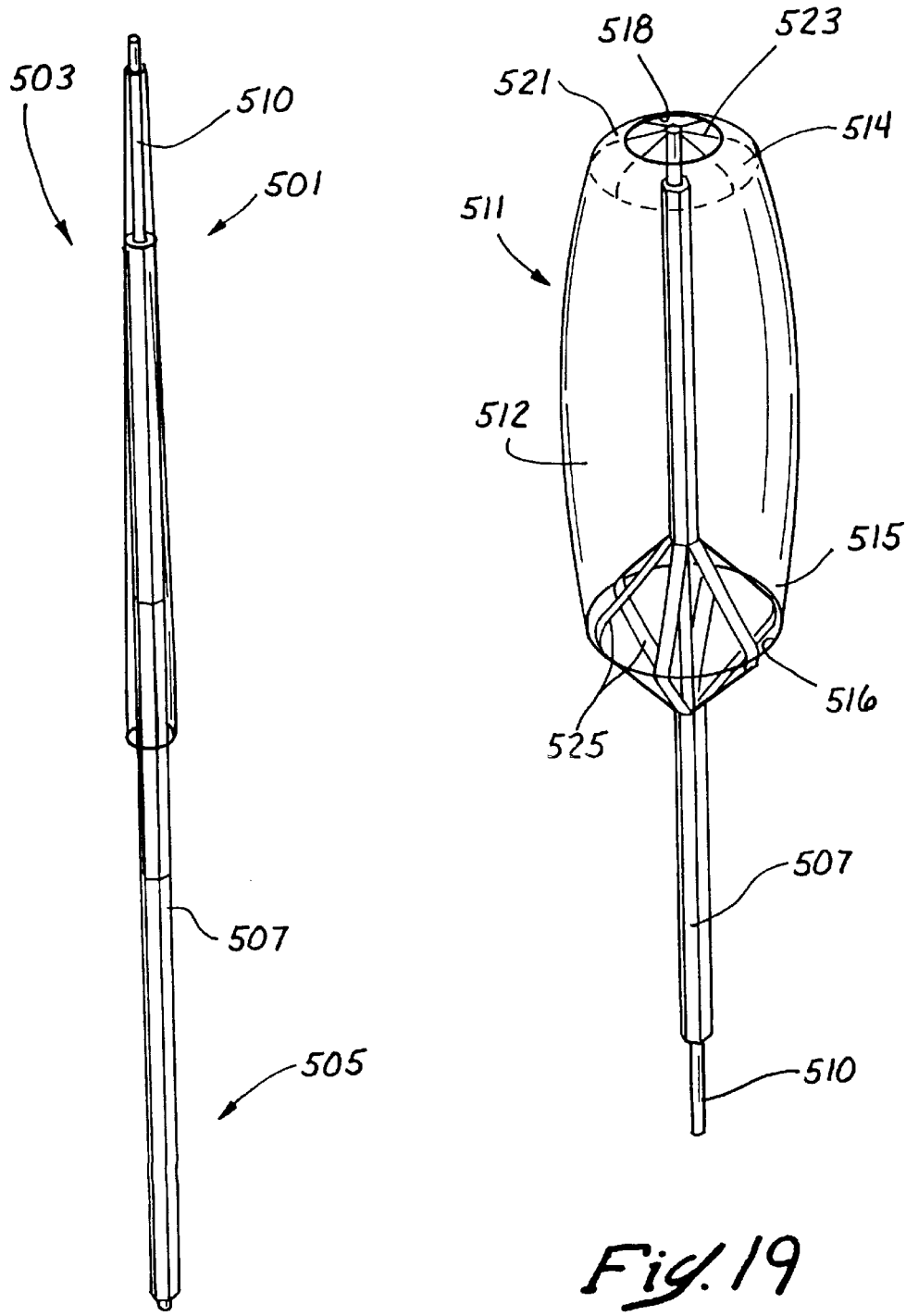

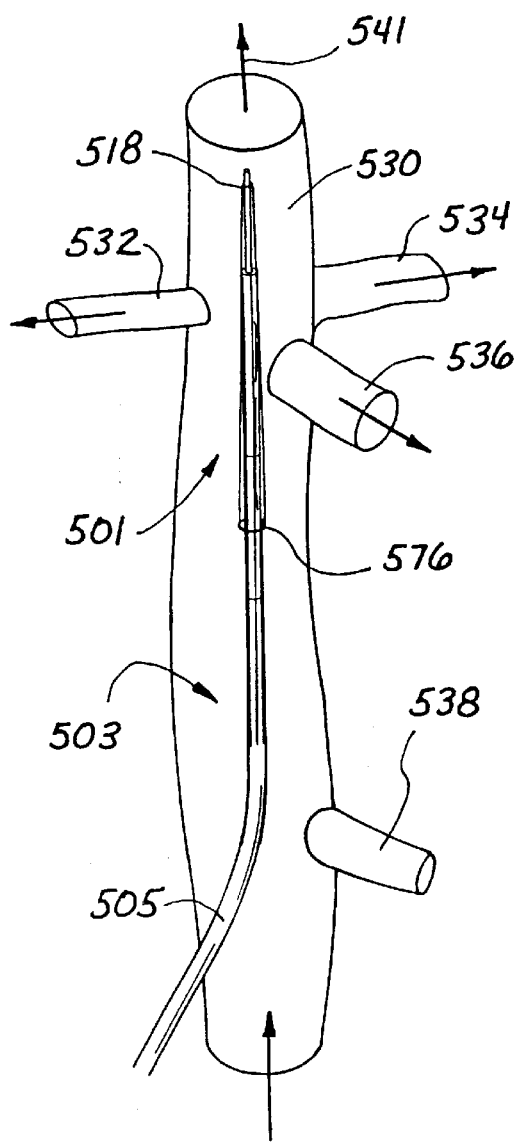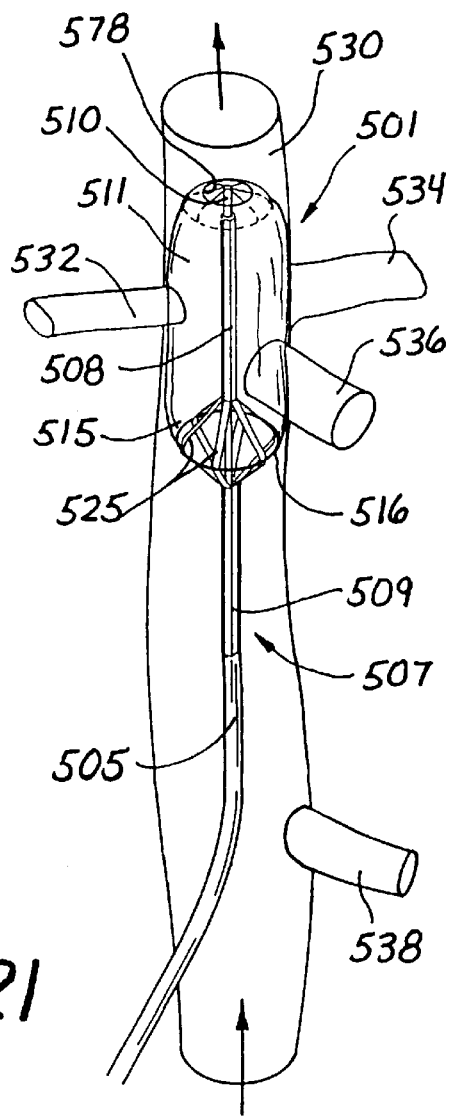
Fig. 20
Fig. 21

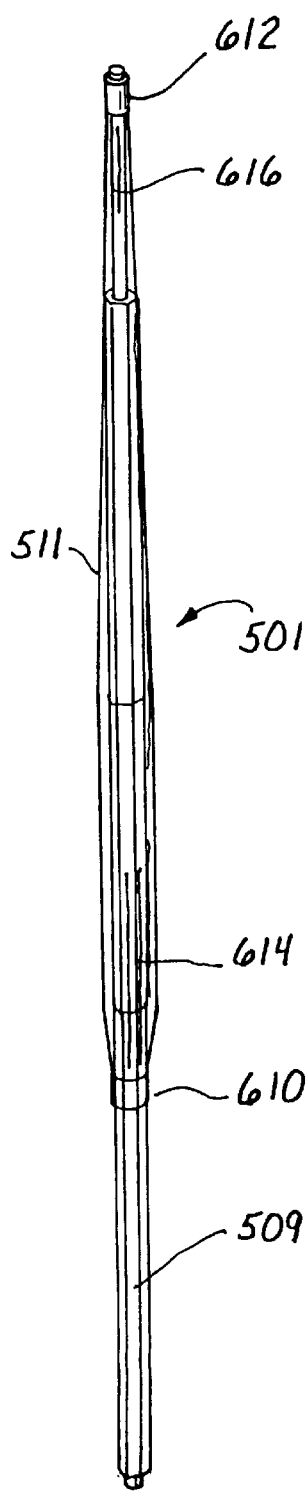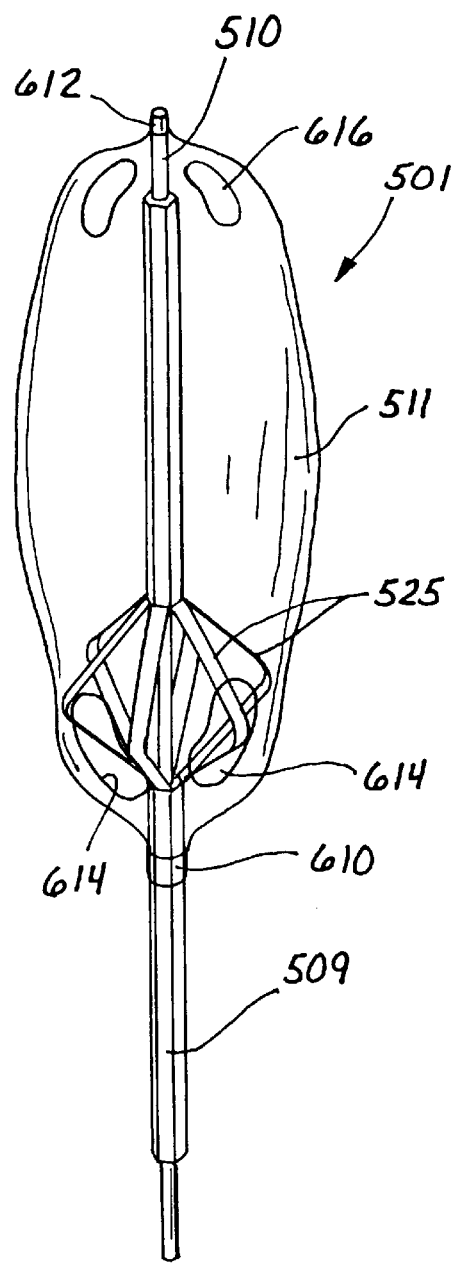
Fig. 22
Fig. 23

PERFUSION-ISOLATION CATHETER APPARATUS AND METHOD

This application claims the benefit of U.S. Provisional No. 60/057,130 filed Aug. 28, 1997.

BACKGROUND

1. Field of the Invention

This invention relates generally to devices for controlling the flow of body fluids in body conduits and more specifically to such devices which can be remotely controlled in a less-invasive procedure.

2. Discussion of the Prior Art

The human body is composed of a labyrinth of body conduits generally organized into various systems of the body. By way of example, a labyrinth of body conduits including the urethra, form the urinary system of the body. Various blood vessels, including the inferior vena cava, are interconnected to form the vascular system of the body. Regardless of the system involved or the particular conduits forming that system, there are many surgical procedures which can benefit from a flow isolator to control flow of a body fluid within the particular system. In general, the flow isolator might function to facilitate the flow of the body fluid in a primary conduit, while inhibiting the flow of that fluid into a secondary conduit. By way of example, hepatic surgery generally requires that the portal vein and hepatic veins be occluded. In the past, this occlusion has been accomplished with cross-clamps which stop the back-flow of blood into the hepatic veins after the portal vein has been clamped.

Unfortunately, there is a significant risk involved in total occlusion of the inferior vena cava. For this reason, this surgery in the past has required that the vena cava be dissected above and below the liver, with the placement of clamps on both sides of the dissection. This has been a time-consuming and a technically challenging part of the procedure. Shunts have also been used to isolate the hepatic veins in similar procedures involving hepatic resection or liver trauma, for example. This procedure is merely representative of many surgical procedures where it is desirable to maintain flow within one body conduit while inhibiting flow in an intersecting conduit.

SUMMARY OF THE INVENTION

The device for the present invention consists of a catheter that is placed intraluminally, either percutaneously or endoluminally. A catheter is disclosed with two primary components, a flow isolator, and an obturator or introducer which facilitates operation of the isolator. In hepatic surgery of the type previously discussed, the catheter is placed into a vessel through a relatively small opening in the wall of the vessel by means of the obturator or introducer which serves to stretch the flow isolator length wise and thereby reduce its profile or diameter. The flow isolator is operatively disposed in the primary conduit, such as the inferior vena cava, and across an intersection with a secondary conduit, such as the hepatic vein. The flow isolator is configured for movement from a low-profile state to a high-profile state which facilitates flow through the primary conduit while inhibiting flow through the secondary conduit. In this manner, primary flow can be facilitated in the primary conduit while inhibiting flow into side-branches, bifurcations, communicating vessels, openings, or wounds.

In one embodiment, the catheter consists of a balloon bonded to a woven or braided tubular structure. The tubular structure serves to support a profusion lumen of the catheter while the balloon is inflated to occlude side-branches or communicators of the vessel. In another embodiment, the flow isolator is in the form of a sleeve having a relatively large opening at its proximal end and a relatively small opening at its distal end. The differential in the size of these openings increases the pressure of the body fluid within the sleeve, opening the sleeve within the primary conduit, but pressing the sleeve against the intersection thereby inhibiting flow in the secondary conduit. In this manner, the sleeve functions as a "wind-sock" as the body fluid itself functions to inflate the sleeve and force it into intimate contact with the inner surface of the primary conduit. While facilitating flow in the primary conduit, the flow isolator inhibits flow into the secondary conduit in order to isolate organs, wounds, or defects such as aneurysms.

Inflation of the sleeve can also be accomplished by providing the sleeve in the form of a plurality of chambers inflatable by an external pressurizing source. Chambers disposed longitudinally of the isolator can be inflated to provide the isolator with a high-profile state. A single circumferential chamber may also be provided at the proximal end in order to enlarge the first opening, thereby facilitating flow of the body fluid into the sleeve.

In another aspect of the invention, a flow isolator is adapted for use in controlling the flow of the body fluid in a primary conduit and a secondary body conduit forming an intersection with the primary body conduit. The flow isolator includes a sleeve having a flexible wall with a proximal end, and a distal end which is preferably disposed to face in the direction of flow of the body fluid in the primary body conduit. The sleeve is adapted for operative disposition within the primary conduit and across the intersection with the secondary body conduit. First portions of the sleeve at the proximal end form a first opening in the wall which facilitates flow of the body fluid into the sleeve. Second portions of the sleeve at the distal end form a second opening in the wall which facilitates flow of the body fluid out of the sleeve. The second opening is smaller than the first opening so as to increase the pressure of the body fluid within the sleeve. This pressure results in inflation of the sleeve whereby the wall is expanded outwardly into contact with the inner surface of the primary conduit. This increases the patency of the primary body conduit facilitating the flow of body fluid within that conduit. It also tends to occlude the intersection with the secondary conduit thereby inhibiting the flow of body fluid within that conduit. In this embodiment, the sleeve is formed to facilitate inflation by the body fluid. Alternatively, it can be formed with chambers which are inflatable to facilitate the high-profile state of the flow isolator.

A further aspect of the invention includes a method for controlling the flow of fluid in a primary conduit, and a secondary conduit forming an intersection with the primary conduit. The method includes the steps of positioning a flow isolator with its proximal ends and distal end disposed on opposing sides of the intersection, and its distal end facing in the direction of normal body fluid flow in the primary conduit. The method further comprises the step of pressurizing the sleeve to force the sleeve against the primary conduit thereby facilitating flow of body fluid within the primary conduit while inhibiting flow of the body fluid in the secondary conduit. In accordance with this method, multiple inflatable chambers can be provided with the method further comprising steps for inflating the chambers to achieve the high-profile state of the flow isolator.

These and other features and advantages of the invention will become more apparent with the description of preferred embodiments and reference to the associated drawings.

DESCRIPTION OF THE DRAWINGS

FIG. 2 is a side view of the balloon catheter of the present invention fully inflated and expanded;

FIG. 3 is an end view of the balloon catheter;

FIG. 9 is a side view of the balloon catheter in its most stretched condition with reduced profile;

FIG. 10 is an enlarged, detailed view of the distal portion of the balloon catheter;

FIG. 18 is a perspective view illustrating an additional embodiment of the invention including a sleeve in a low-profile state;

FIG. 19 is a perspective view of the embodiment of FIG. 18 with the sleeve in a high-profile state;

FIG. 20 is a perspective view of the FIG. 18 embodiment disposed in the low-profile state in the primary body conduit;

FIG. 21 is a perspective view of the FIG. 19 embodiment disposed in the high-profile state in the primary body conduit;

FIG. 22 is a perspective view of an additional embodiment of the invention including elliptical holes and illustrated in a low-profile state;

FIG. 23 is a perspective view of the FIG. 22 embodiment in a high-profile state;

DETAILED DESCRIPTION

Figure 1:
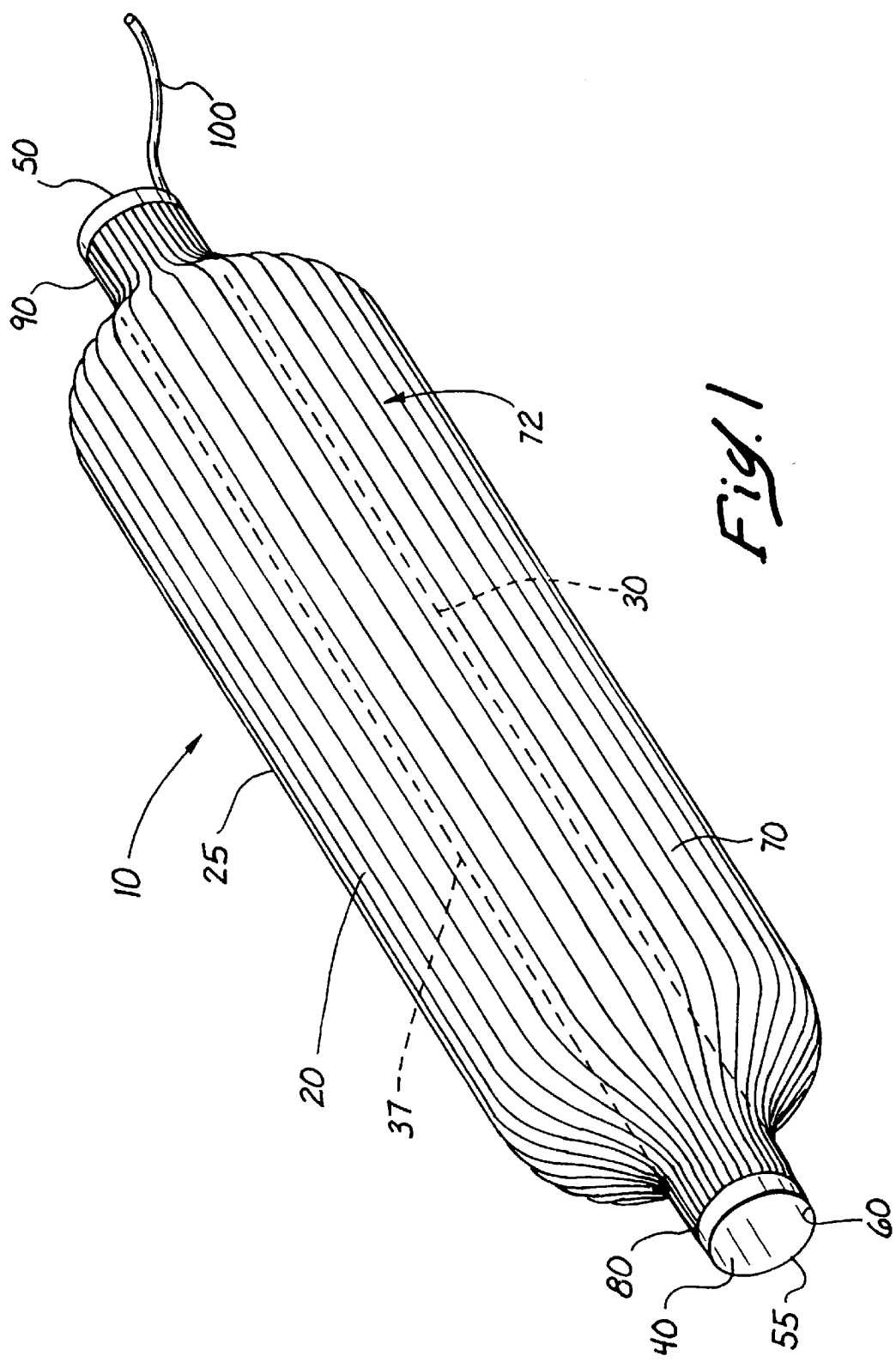
FIG. 1 is a perspective view of the balloon catheter of the present invention fully inflated and expanded.
Figure 4:
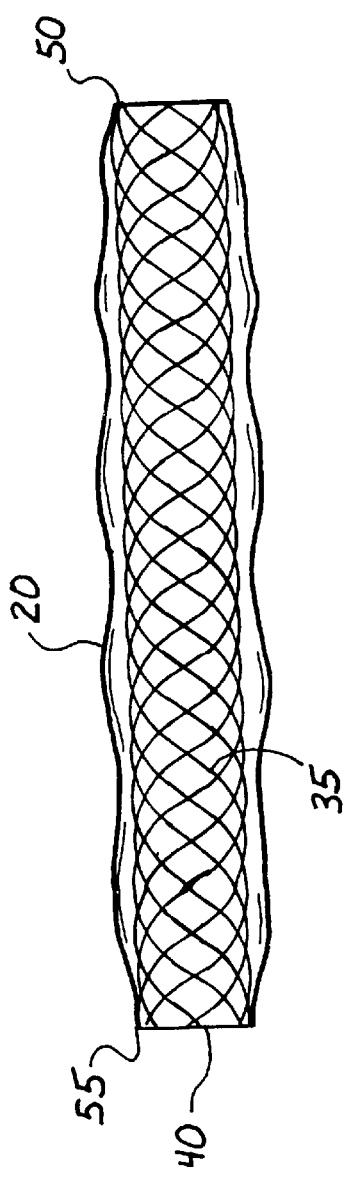
FIG. 4 is a side view of the balloon catheter with the balloon at rest.
Figure 5:
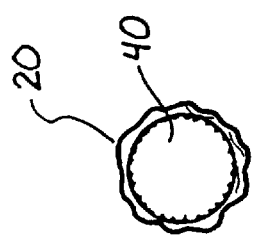
FIG. 5 is an end view of the balloon catheter with the balloon at rest.
Figure 6:
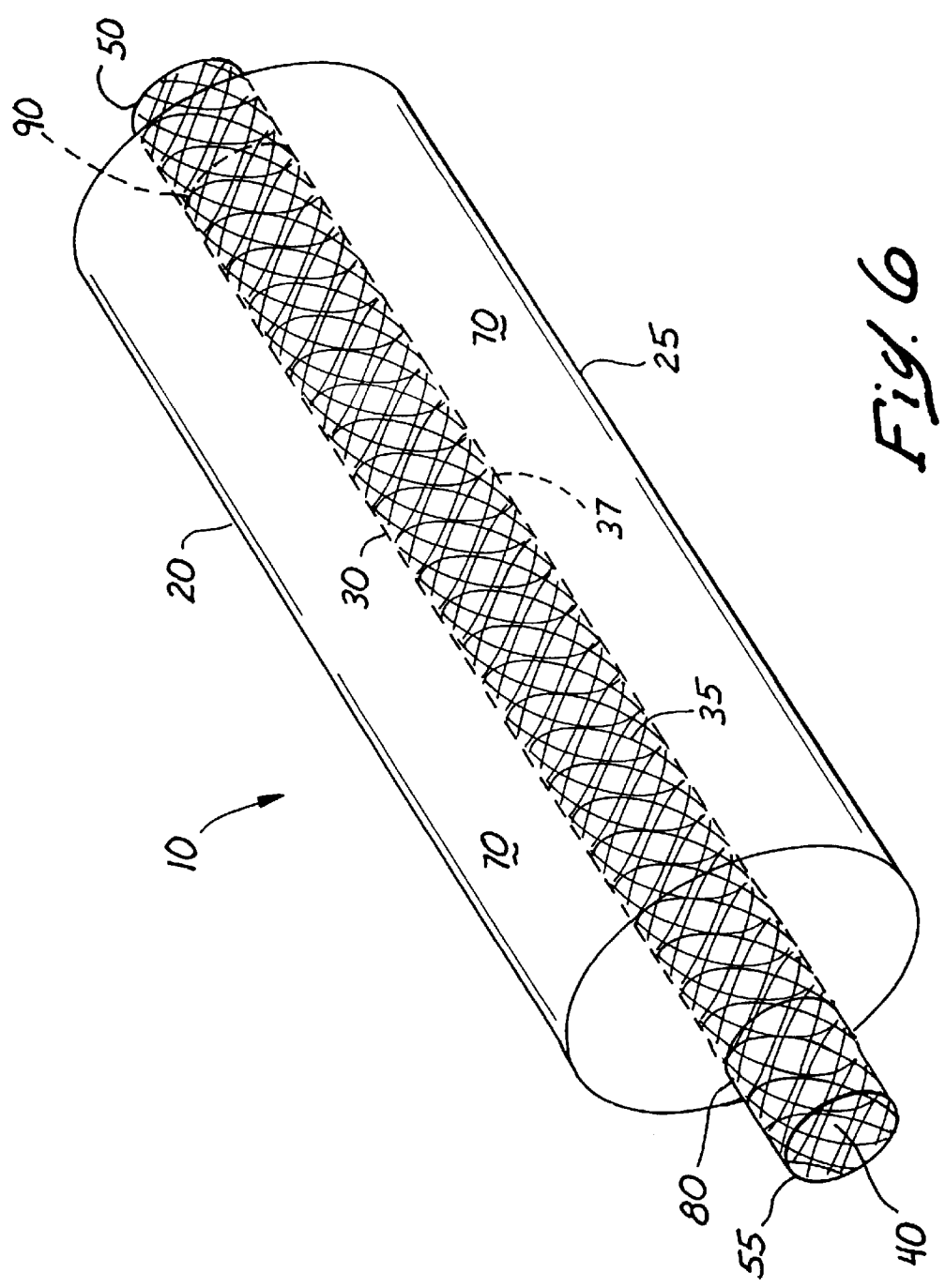
FIG. 6 is a perspective view of the structure of the through-lumen section of the balloon catheter.
Figure 7:
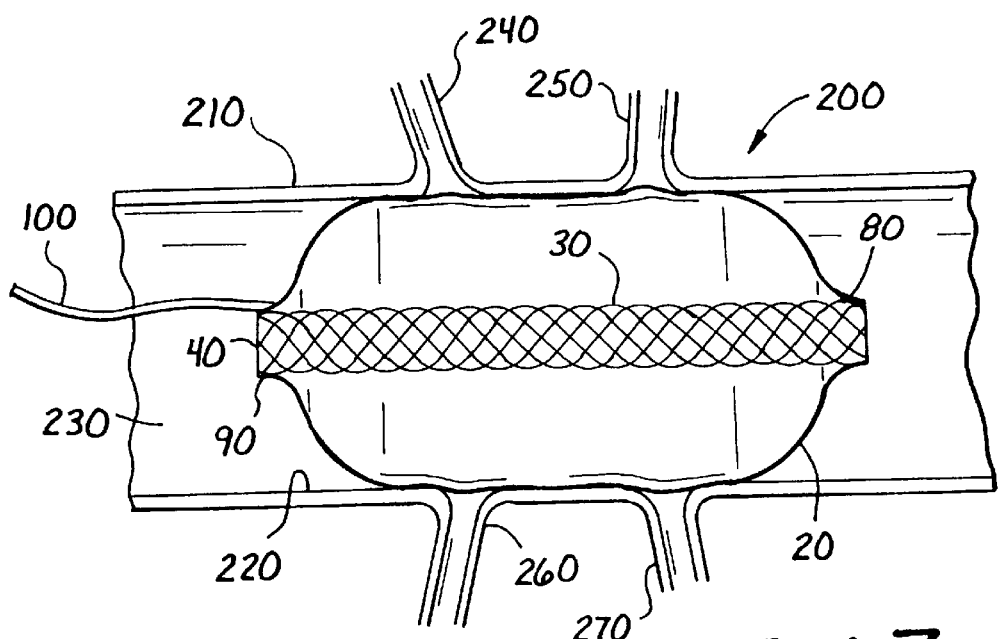
FIG. 7 is a side view of the inflated balloon catheter within a body passage.
Figure 8:
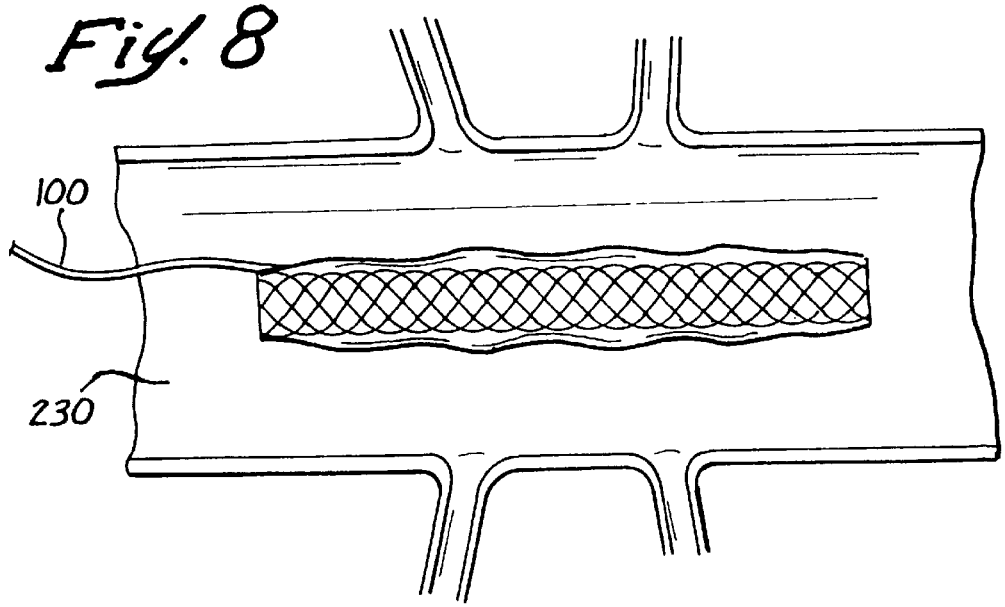
FIG. 8 is a side view of the un-inflated balloon catheter within a body passage.
Figure 12:
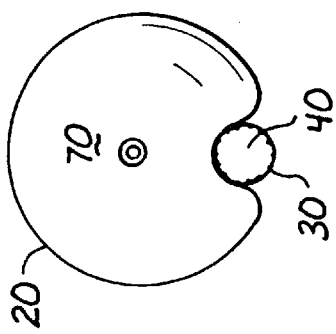
FIG. 12 is an end-elevation view of the low-profile catheter illustrated in FIG. 11.
Figure 14:
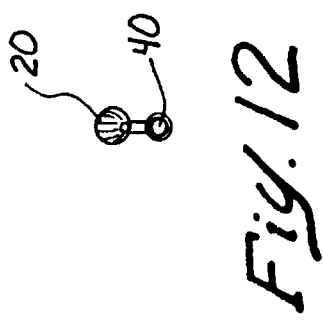
FIG. 14 is an end-elevation view of the catheter illustrated in FIG. 13.
Figure 13:
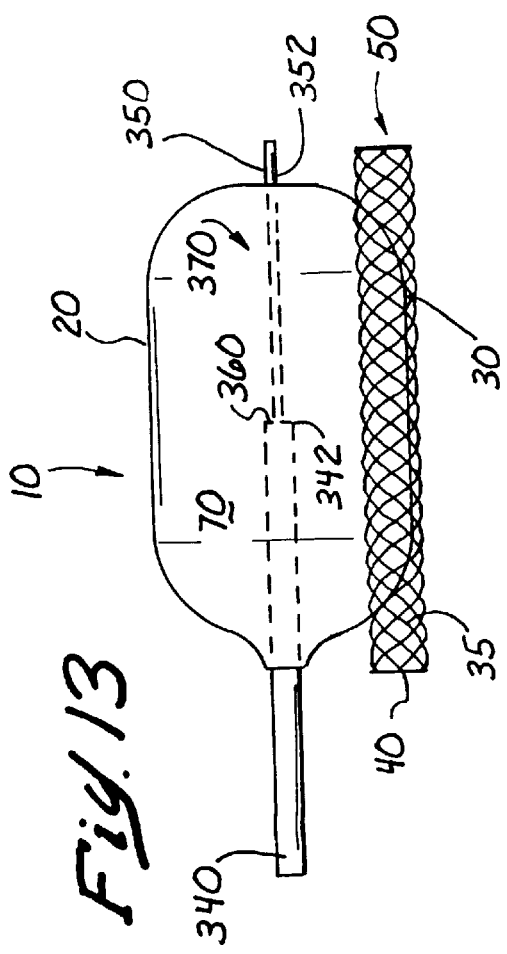
FIG. 13 is a side-elevation view of the catheter of FIG. 11 illustrated in an inflated high-profile state.

With reference to FIG. 1–10, there is shown a through-lumen balloon catheter 10 consisting of a woven or braided support structure or tube 30 which forms the inner wall 37 of the inflatable portion 72 of the catheter 10 and an impermeable elastomeric outer wall 25 which forms the outer portion of a balloon 20. The proximal portion 90 of the balloon material is bonded to the proximal end 50 of the tubular inner structure 30 and the distal end 80 of the balloon material is bonded to the distal end 80 of the tubular inner structure 30. An inflation tube 100 is provided to inflate the balloon 20.

The support structure 30 provides a relatively non-compressible lumen 40 when compared to the structure of the outer wall 25. This configuration allows for a balloon 20 that can be inflated within a body passage 200 (FIG. 7) to provide occlusion of said passage 200 while providing a pathway through the lumen 40 for the passage of fluid. In this manner, side branches 240, 250, 260, 270 may be denied fluid flow while fluid flow to other vital structures is maintained.

The balloon 20 and the support tube 30 may be stretched in length, FIG. 9, thereby reducing the profile or diameter of the catheter 10. The reduced profile assists in the introduction of the catheter through small incision sites or introducers. The woven or braided tubular structure 30 may be stretched by means of an obturator or introducer stylet 300 which consists of an engagement feature 330 that engages filaments 35 at a distal end 55 of the tubular structure 30. As the distance between a proximal end 50 of the braided tube 30 and the distal end 55 of the braided tube 30 is increased, the profile of the catheter 10 is reduced. As that distance is reduced, the profile or diameter increases.

In use, the catheter 10 may be placed into a vessel or body passage 200 while stretched to a minimum diameter. The catheter 10 may be released from the stylet or obturator 300 and allowed to return to a normal or relaxed diameter. The inflatable balloon 20 may then be advanced into position within the lumen 230 and adjacent to side branches that are to be isolated from the flow of the passage or vessel 200. The inflatable balloon 20 may then be inflated by filling the space 70 between the impermeable braided support tube 30 and the outer balloon skin 25 through the inflation tube 100. To remove the catheter 10 from the vessel 200, the obturator or stylet 300 may be reinserted into the tubular support 30. The proximal end 50 of the support 30 and the distal end 55 of the support 30 are separated thereby reducing the profile so that the device may be removed as inserted.

An alternate embodiment of the present invention is shown in FIGS. 13 through 16 where the balloon 20 is formed on two coaxial tubes 340, 370 that are sized and configured to slide with respect to each other. The balloon 20 is positioned at a distal end 342 of the outer tube 340, and at a distal end 352 of the inner tube 350 in a manner which permits the inner tube 350 to be extended from the distal end 360 of the outer tube 340, in order to stretch the balloon 20 to a low profile. The flow through channel or lumen 40, which is provided by the woven or braided tubular support structure 30, is carried off-axis to one side of the balloon 20.

Both the balloon 20 and the support structure 30 are stretched to a low-profile by extension of the inner tube 350 relative to the outer tube 340. When the balloon 20 and the tube 30 are allowed to assume an "at rest" condition, their diameters naturally expand. In addition, as the balloon 20 is inflated, it further shortens in length which, in turn, forces the attached support tube 30 to also increase in diameter.

Figure 11:
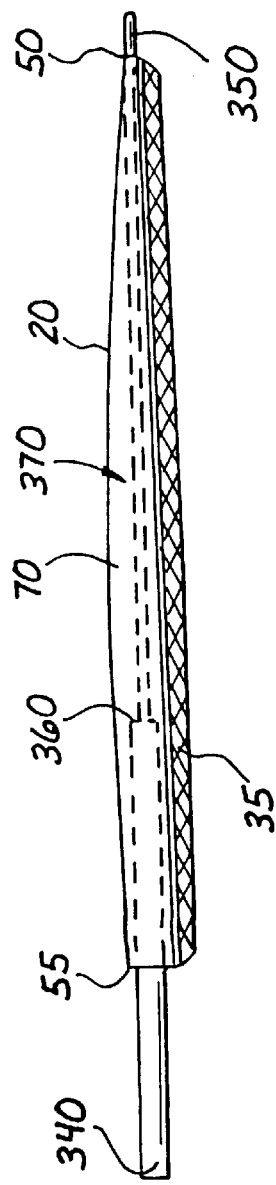
FIG. 11 is a side-elevation view of a further embodiment of the invention illustrating the catheter in a low-profile state.
Figure 15:
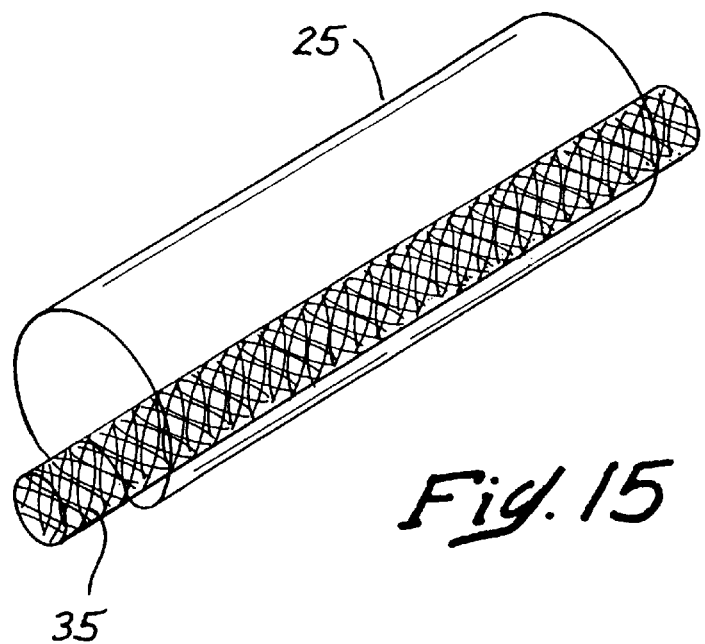
FIG. 15 is a perspective view of the embodiments of FIGS. 11–14, illustrating the balloon with an off-axis profusion channel.
Figure 16:
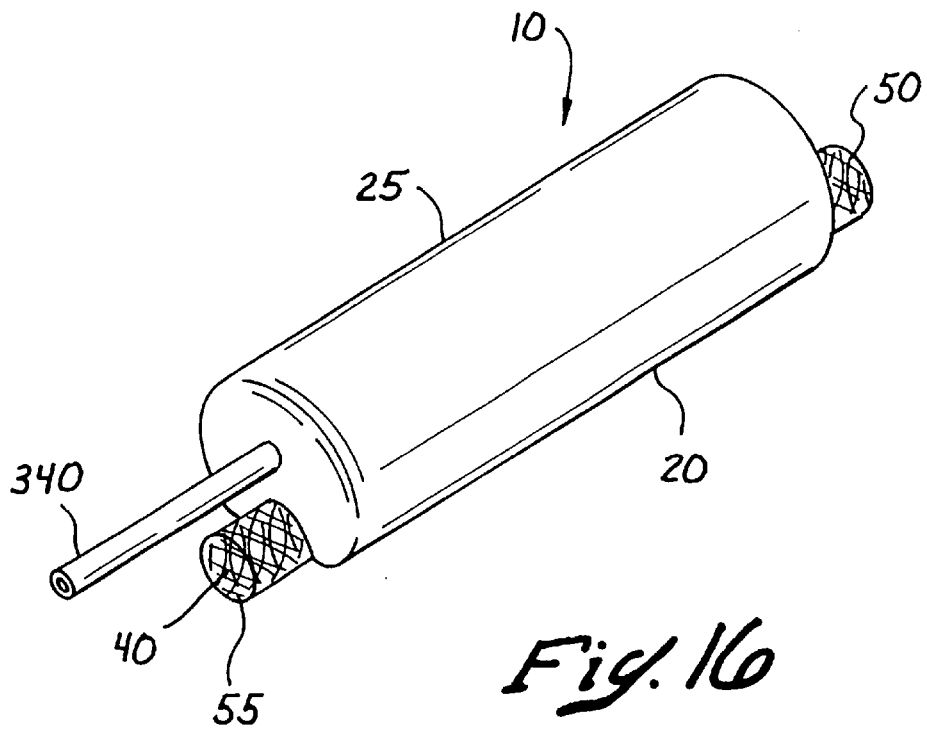
FIG. 16 is a perspective view similar to FIG. 15 and illustrating the balloon and profusion channel apparatus mounted on inner and outer co-axial tubes.

When inflated, the balloon 20 forms an occlusive bladder which isolates the side branches of a body passage in the area of engagement. The adjacent area, where the support tube 30 resides, forms a flow-through passage between the balloon 20 and the body passage wall. This assembly requires only that the support tube 30 be attached to the balloon 20 rather than co-axially constructed as part of the balloon 20. In use, the balloon 20 and the tube 30 can be inserted into the operative position in a low-profile, highly elongated or stretched condition, FIG. 11, through an introducer sheath. Some of the advantages associated with this embodiment include the following:

the tube 30 does not need to be fluid tight or coated,
the tube 30 is more stretchable when not coated,
the balloon 20 may be very thin and compliant,
the catheter 10 is easy to assemble, and
the diameter of tube 30 can be set by braid pitch.

Figure 17:
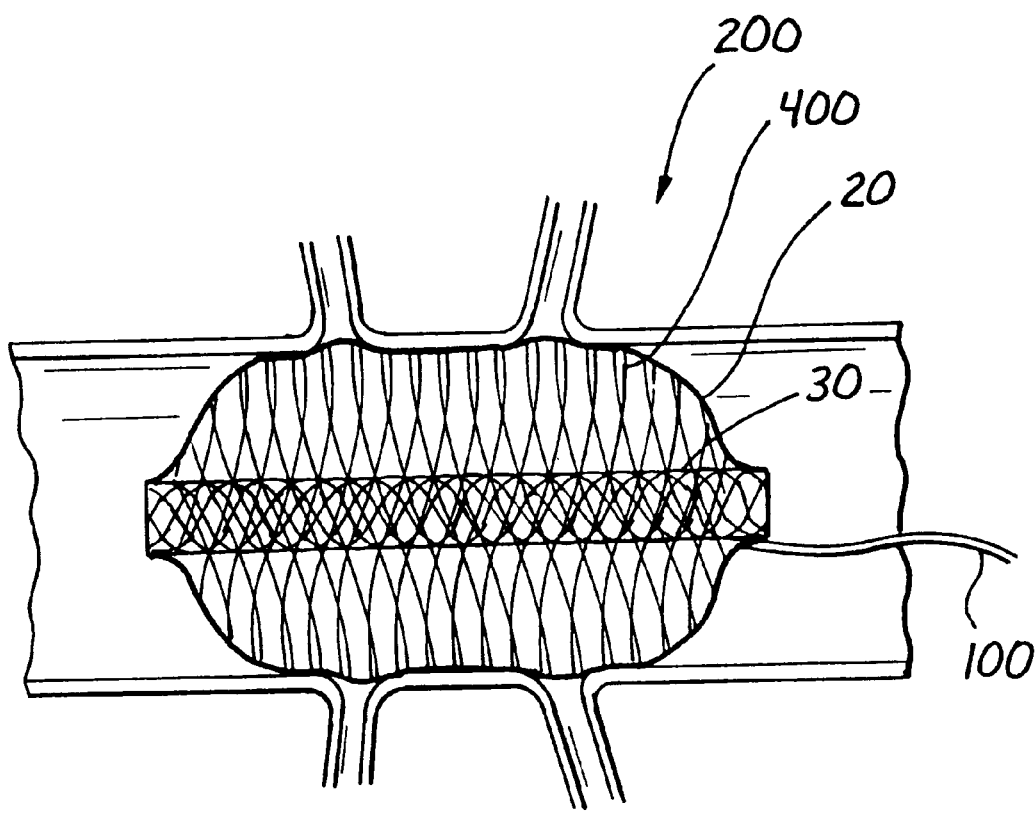
FIG. 17 is a side-elevation view of an embodiment having a braid over the balloon.
Figure 24:
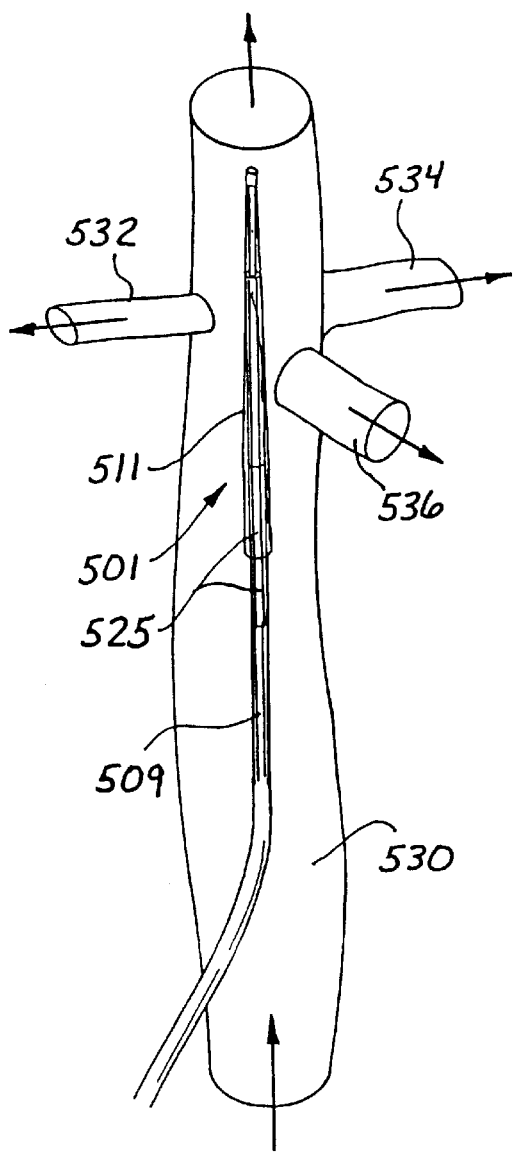
FIG. 24 is a perspective view of the FIG. 22 embodiment disposed in the low-profile state in the primary body conduit.
Figure 25:
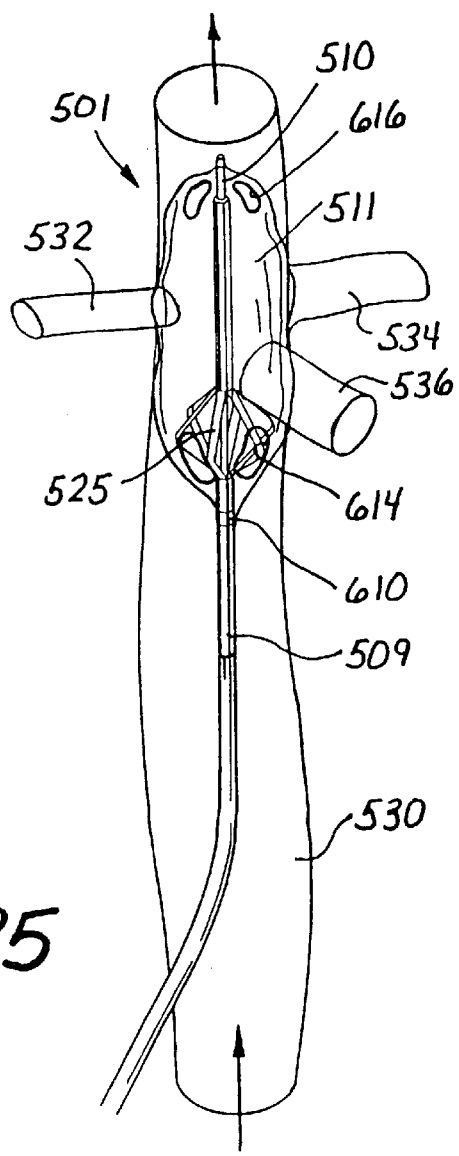
FIG. 25 is a perspective view of the FIG. 23 embodiment disposed in the high-profile state in the primary body conduit.

An alternate embodiment of the occlusion balloon 20 is illustrated in FIG. 17 to include a woven fabric or mesh 400 which covers the exterior of the balloon 20. The fabric may be integral to the balloon material or, in a preferred embodiment, independent of it. The independent fabric construction is more likely to stretch axially to a low-crossing profile or diameter, than it would with an integral or composite construction. In addition, the independent construction allows for small fluctuations or small movements of the balloon 20 without breaking surface contact between the fabric 400 and the wall of the vessel 200.

In many procedures it is important that atraumatic traction be provided as a component of an occlusion balloon 20 so that excessive fluid pressure is not required to maintain the preferred position of the balloon 20 within the vessel 200. However, simply texturing a balloon is not adequate particularly for occlusion balloons that have a high-inflation ratio. The texture of such a balloon diminishes exponentially with inflation. By comparison, the texture of the expandable woven fabric 400 is relatively constant regardless of the inflated profile of the balloon 20.

An additional benefit achieved by use of the fabric 400 is realized during placement and removal of the balloon 20. During this process, the fabric 400 assists in reducing the profile of the balloon 20 itself by imposing a radially-compressive load. The fabric 400 also reduces the friction between the balloon material and the vessel wall. Lubricants or fluids may be added to this construction where they are maintained within the interstices of the fabric and not easily wiped from the surface, as would be the case with an ordinary balloon.

Further advantages associated with this embodiment include:

a reduced-crossing profile,
increased stability without over-inflation,
increased strength,
predictable sizing of the balloon 20, and
facilitated lubrication or drug delivery.

Another embodiment of the invention is illustrated in FIGS. 18–21 where a flow isolator is designated by the reference numeral 501. This flow isolator 501 is mounted at the distal end of a catheter 503 having a shaft 505 formed of co-axial elements such as an outer tube 507 and an inner tube 510. The outer tube 507 includes a distal portion 508 that is fixed to the inner tube 510 and a proximal portion 509 which is slideable on the inner tube 510.

In this embodiment, the flow isolator 501 is provided in the form of a sleeve 511 having a lateral wall 512 which extends longitudinally, and an end wall 514 which extends generally radially. At the proximal end of the sleeve 501, portions 515 of the lateral wall 512 define a hole 516 which provides fluid access into the sleeve 511. A similar hole 518 is formed at the distal end of the sleeve 511 by portions 521 of the end wall 514. The portions 521 preferably attach to the inner tube 510 of the catheter shaft 505, for example, by a plurality of tethers 523 which extend between the end wall 514 and the inner tube 510. In a similar manner, a plurality of fingers 525 connect the outer tube 507 to the portions 515 of the lateral wall 512 which define the opening 516. With this construction, axial movement of the inner tube 510 relative to the outer tube 507 causes the flow isolator 501 to move between a low-profile state, illustrated generally in FIG. 18 and a high-profile state illustrated generally in FIG. 19.

This structure is particularly adapted for use in a primary conduit such as that designated by the reference numeral 530 in FIGS. 20 and 21. The primary conduit 530 forms intersections with each of a plurality of secondary conduits such as those designated by the reference numerals 532, 534, 536, and 538. By way of example, the primary conduit 530 may be the inferior vena cava, while the secondary conduits 532–536 might be hepatic veins leading to the liver (not shown). The secondary conduit 538 might be a renal vein. In this case, use of the flow isolator 501 would be intended to facilitate a flow of blood through the inferior vena cava 530 and the secondary renal vein 538 while inhibiting blood flow through the secondary hepatic veins 532–536.

This is accomplished in a preferred method by initially inserting the catheter 503 into the inferior vena cava 530 in the low-profile state, as illustrated in FIG. 20. Note that the catheter 503 is preferably inserted distally in the direction of blood flow, as shown by the arrow 541. The catheter 503 is then positioned with the primary hole 216 oriented to face proximally of the veins to be isolated (such as the veins 532–536) and the secondary hole 218 positioned to face distally of the secondary conduits 532–536. With this procedure, the blood flow between the inferior vena cava 530 and the secondary renal vein 538 is not inhibited.

Once the flow isolator 501 is appropriately positioned, it can be expanded to the high-profile state, as illustrated in FIG. 21. This is accomplished by inflating the sleeve 511, in this case using the blood flow within the vena cava. Inflation can be achieved, for example, by enlarging the primary hole 516 at the proximal end of the isolator 501. This is accomplished in a preferred method by moving the inner tube 510 proximally of the outer tube 507 thereby expanding the fingers 525 radially outwardly.

In a preferred embodiment, the fingers 525 carry the portions 515 outwardly to the inner surface of the vena cava 530. This provides the opening 516 with a diameter generally equivalent to the inner diameter of the vena cava 530. The fingers 525 will typically be formed of the same material as the outer tube 507 and provided with living hinges which facilitate radial expansion in a known manner. Once the hole 516 is enlarged, blood flowing within the vena cava 530 will enter the sleeve 511. This blood will pass from the sleeve 511 through the second hole 518 at the distal end of the isolator 501.

In the illustrated embodiment, the primary hole 516 has a diameter which is greater than the secondary hole 518. As a consequence, the pressure of the blood within the sleeve 511 tends to increase. This forces the walls of the sleeve outwardly against the inner surface of the vena cava 530, thereby inhibiting blood flow into the secondary hepatic veins 532–536. Note that when the flow isolator 501 is operatively disposed in its high-profile state, as illustrated in FIG. 21, the flow of blood through the vena cava 530 is facilitated as is the flow of blood into the secondary renal vein 538. While this flow of blood is advantageously maintained by the isolator 501, the flow of blood into the secondary hepatic veins 532–536 is substantially blocked, thereby inhibiting the flow of blood to the liver (not shown).

In the foregoing embodiment, the primary hole 516 and the secondary hole 518 are preferably defined in respective radial planes and are co-axial with the shaft 505 of the catheter 503. In an additional embodiment illustrated in FIGS. 22–25, the sleeve 501 is formed with a proximal end 610 which is fixed to the portion 509 of the outer tube 507, and a distal end 612 which is fixed to the inner tube 510. In this embodiment, the lateral wall 512 extends between the ends 610 and 612.

With this configuration, the primary hole 516 can be formed as a plurality of elliptical openings 614, and the secondary hole 518 can be formed as a plurality of elliptical openings 616. With the fingers 525 disposed within the sleeve 501 between the ends 610 and 612, it is preferable that the elliptical opening 614 be configured to extend between the fingers 525.

Figures 30, 31:
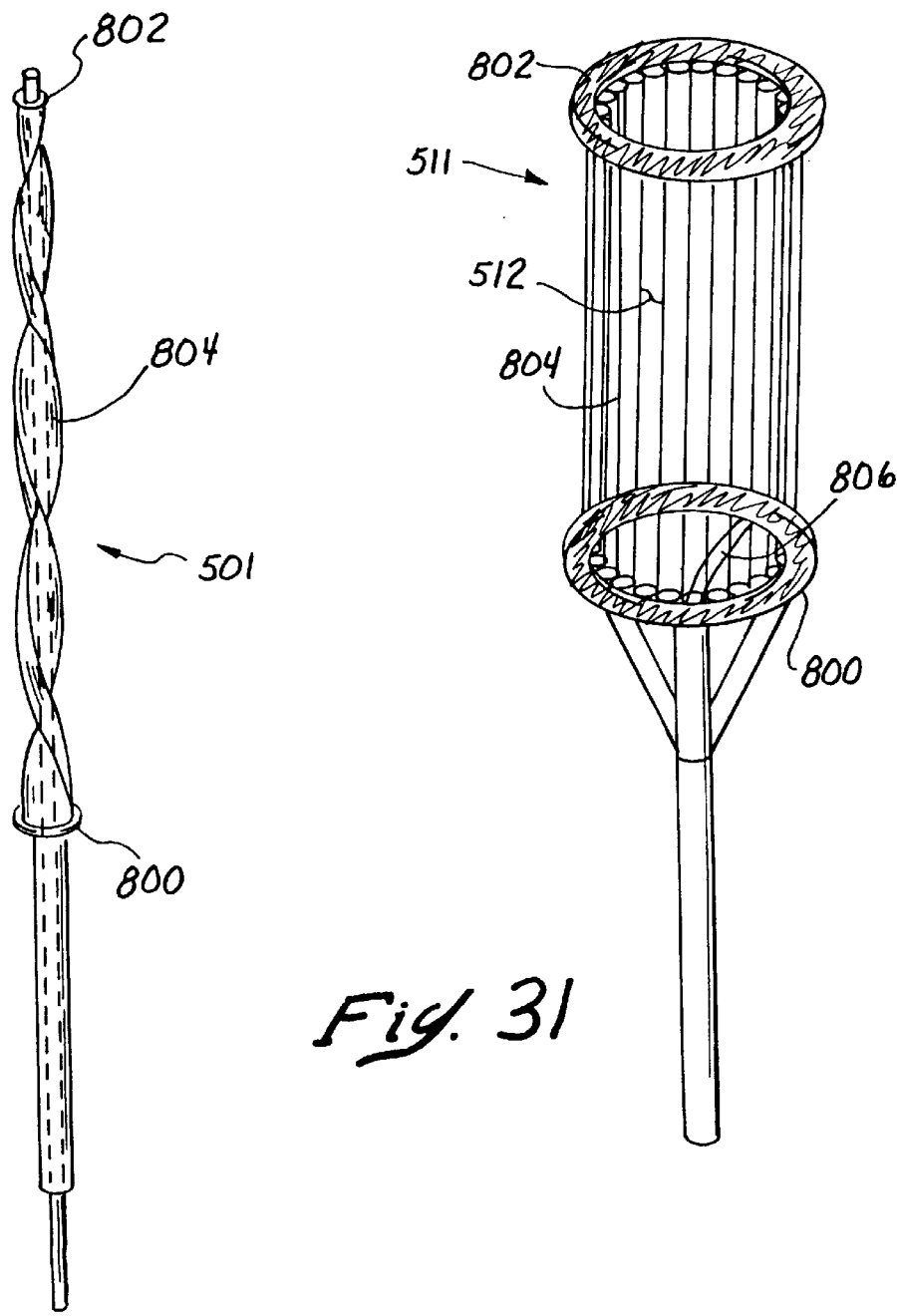
FIG. 30 is a perspective view of a further embodiment of the invention including a plurality of inflatable chambers, and illustrated in the low-profile state.
FIG. 31 is a perspective view of the FIG. 30 embodiment in a high-profile state.

In a comparison with the prior embodiment, this configuration provides a cleaner, low-profile state, as illustrated in FIG. 30, in that the fingers 525 are generally covered by the sleeve 511. As in the previous embodiment, it is desirable to provide the primary elliptical holes 614 with a larger area than that of the secondary elliptical holes 616. This facilitates pressurization and inflation of the sleeve 511 in the manner previously discussed.

A further embodiment of the invention, as illustrated in FIGS. 26–29, wherein the sleeve 511 of the isolator 501 is provided with a circumferential chamber 700 around the proximal opening or hole 516. With this exception, this embodiment of FIG. 26 will have many of the features previously discussed with respect to the previous embodiments.

In this embodiment, the chamber 700 functions much as the fingers 525 in the FIG. 18 embodiment. To that end, it provides a structure which can move between a low-profile state and a high-profile state. In this case, the structure includes an inflation tube 702, which extends to the proximal end of the catheter and permits deflation of the chamber 700 to achieve the low-profile state, and inflation of the chamber 700 to achieve the high-profile state.

In the high-profile state, the chamber 700 functions to enlarge the opening 516 in order to facilitate receipt of the body fluid into the sleeve 511. To that end, it is desirable that the opening 516 be provided with a diameter substantially equivalent to the inside diameter of the primary conduit 530. Although this could be achieved with an elliptical chamber 700, the smallest structure providing the opening 516 with this diameter would be a circular chamber 700 oriented to extend radially of the primary conduit 530 and the shaft 505 of the catheter 503. With this orientation, the opening 516 is formed in a radial plane and provided with a diameter substantially equivalent to that of the inner diameter of the conduit 530. The preferred orientation of the chamber 700 relative to the shaft 505 can be maintained by a plurality of tethers 704 extending between the proximal end of the isolator 501 and the shaft 505. These tethers 40 not only tend to fix the chamber 700 in the radial plane, but also to fix that radial plane at a preferred operative position along the shaft 505.

When the isolator 501 is operatively positioned in the primary conduit 530, the chamber 700 is inflated to facilitate flow of the body fluid into the sleeve 500. This fluid then flows from the sleeve 511 and through the distal hole 518 in a manner previously discussed. While maintaining the hole 518 at a diameter less than that of the hole 516, the blood tends to pressurize the isolator 501 forcing its lateral wall 512 against the inner surface of the conduit 530. This tends to effectively isolate the secondary conduit, such as the hepatic vessels 532–536, in a manner previously described.

Still a further embodiment of the isolator 501 is illustrated in FIGS. 30–33. This embodiment is also adapted to move between a low-profile state facilitating insertion of the catheter 503, and a high-profile state facilitating isolation of the secondary conduit, such as the vein 532, from the primary conduit, such as the vena cava 530.

As best illustrated in FIG. 31, the isolator 501 of this embodiment includes a circumferential chamber 800 at the proximal end, and a circumferential chamber 802 at the distal end of the isolator 501. These chambers 800 and 802 are in fluid communication with a plurality of longitudinal chambers 804, which form the lateral wall 512 of the sleeve 511. In a preferred embodiment, the chambers 800, 802, and 804 are in fluid communication with each other thereby facilitating simultaneous inflation of the structures.

Figure 33:
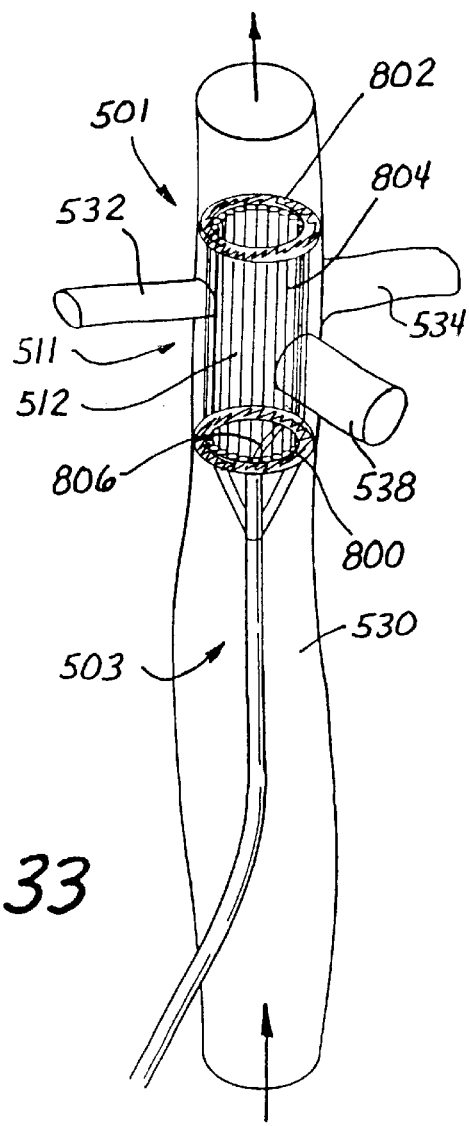
FIG. 33 is a perspective view of the FIG. 31 embodiment disposed in the high-profile state in the primary body conduit.

When the flow isolator 501 is operatively disposed in the primary conduit 530, as illustrated in FIG. 33, it can be inflated through an inflation tube 806 to place the isolator 501 in its high-profile state. In this state, best illustrated in FIG. 33, the inflated chamber 800 forms a seal with the inner wall of the primary conduit 530. This seal is preferably formed upstream from any secondary conduits, such as the hepatic veins 532–536, which are selected for isolation.

Inflating the isolator 501 also enlarges the chamber 802 at the distal end. This also enables the chamber 802 to form a seal at the distal end of the isolator 501, preferably downstream from the conduits to be isolated, such as the hepatic veins 532–536. Having formed a seal at the chambers 800 and 802, it can now be seen that the longitudinal chambers 804 serve several functions. First, the chambers 804 form the sleeve 511 which then defines a secondary conduit or shunt between the seals at the chambers 800 and 802. This facilitates the flow of body fluids, such as blood, through the primary conduit, such as the inferior vena cava 530. In this respect, the sleeve 511 functions as an endoluminal shunt providing a secondary passage which maintains the flow of fluid around the secondary conduits 532–536. This shunt, of course, is disposed within the primary conduit 530 in this case.

In addition to forming the sleeve 511, the longitudinal chambers 804 also function to axially separate the circumferential chambers 800 and 802. This provides the isolator 501 with a predetermined size sufficient in length to isolate all of the secondary conduits desired.

Figure 26:
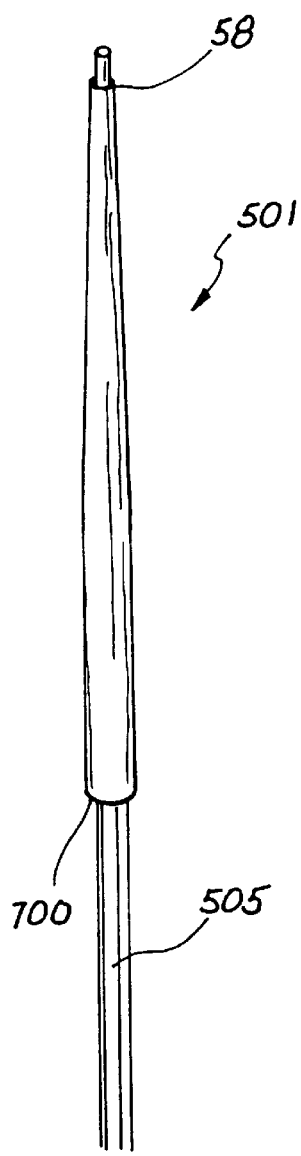
FIG. 26 is another embodiment of the invention having an inflatable circumferential chamber and illustrated in a low-profile state.
Figure 27:
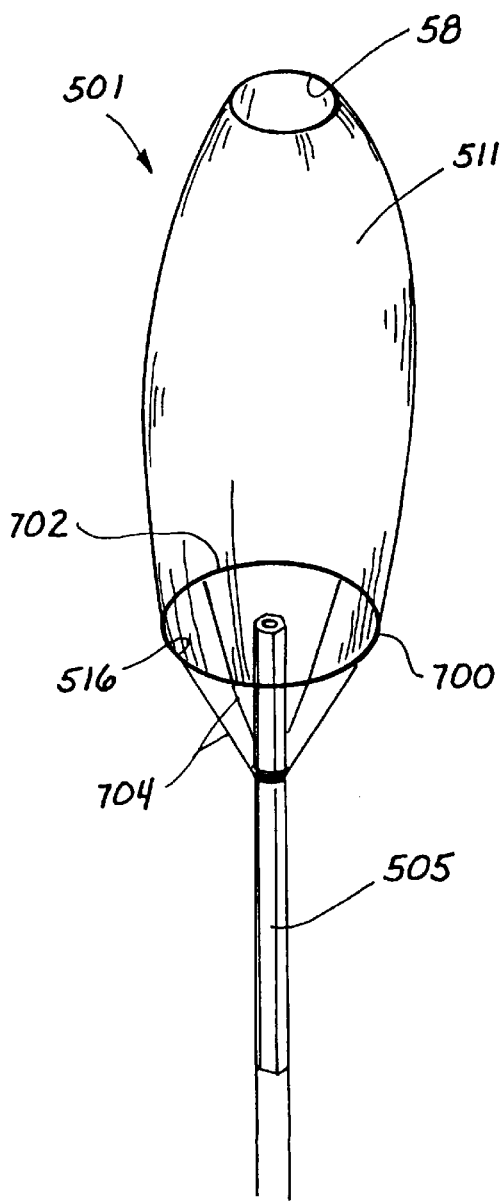
FIG. 27 is a perspective view of the FIG. 26 embodiment in a high-profile state.
Figure 28:
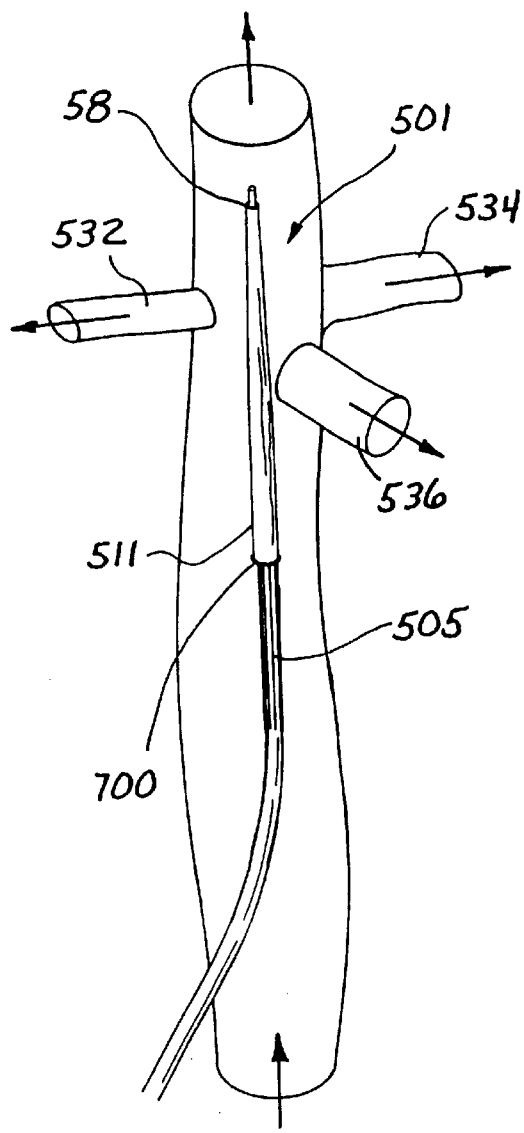
FIG. 28 is a perspective view of the FIG. 26 embodiment disposed in the low-profile state in the primary body conduit.
Figure 29:
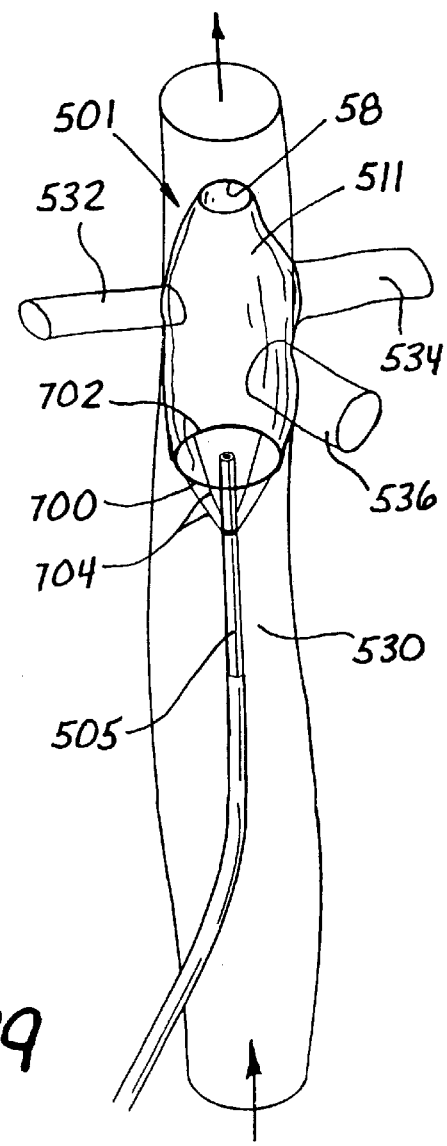
FIG. 29 is a perspective view of the FIG. 27 embodiment disposed in the high-profile state in the primary body conduit.

Having explained the function of the isolator 501 in this embodiment, it will now be apparent that it differs in several respects from the embodiment of FIG. 26. For example, although the circumferential chambers 700 and 800 share some elements of similarity, it will be noted that the chamber 700 in the FIG. 26 embodiment does not necessarily form a seal with the inner wall of the primary conduit 530. This seal formed by the chamber 800 is an important characteristic of the FIG. 30 embodiment. Additionally, the isolator 501 of the FIG. 26 embodiment is inflated by the body fluids, such as blood, which forces the sleeve 511 against the inner wall of the primary conduit 530. In the embodiment of FIG. 30, the sleeve 511 does not necessarily isolate the secondary conduits 532–536. This isolation is achieved by the seals formed between the chambers 800, 802, and the inner surface of the primary conduit 530.

Figure 32:
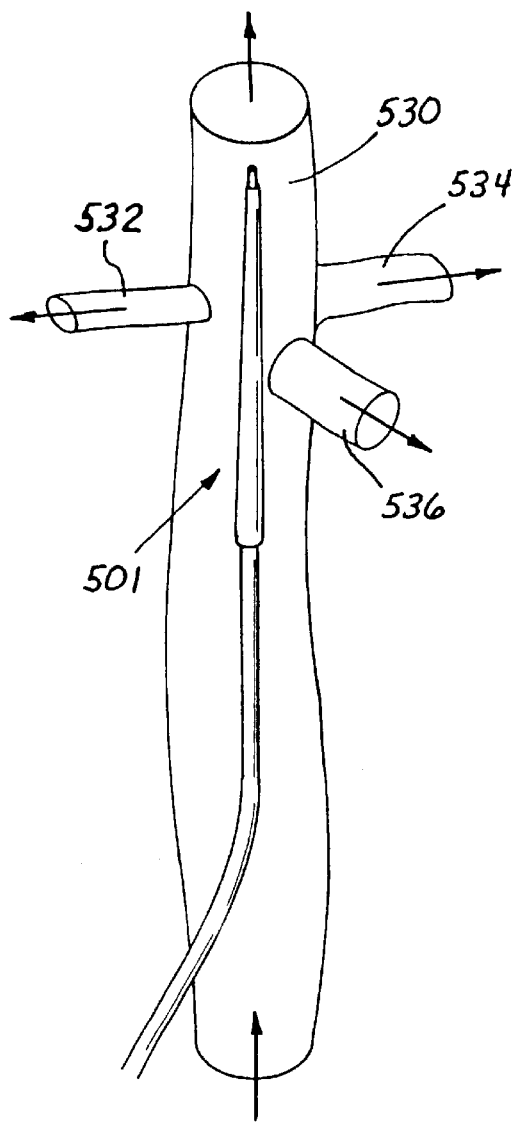
FIG. 32 is a perspective view of the FIG. 30 embodiment disposed in the low-profile state in the primary body conduit.

As a further distinction, it will be noted that the sleeve 511 of the FIG. 30 embodiment is not pressurized by the body fluid, but rather by an external fluid, such as air, through the inflation tube 806. Although the function of the sleeve 511 in the FIG. 30 embodiment could be accomplished by a single rigid tube or a multiplicity of smaller tubes, this would greatly inhibit introduction of the catheter 503. For this reason, the longitudinal chambers 804 forming the sleeve 511 are formed from a flexible material such as polyethylene. This material can be twisted or otherwise held in a low-profile state, as illustrated in FIG. 32.

Figure 36:
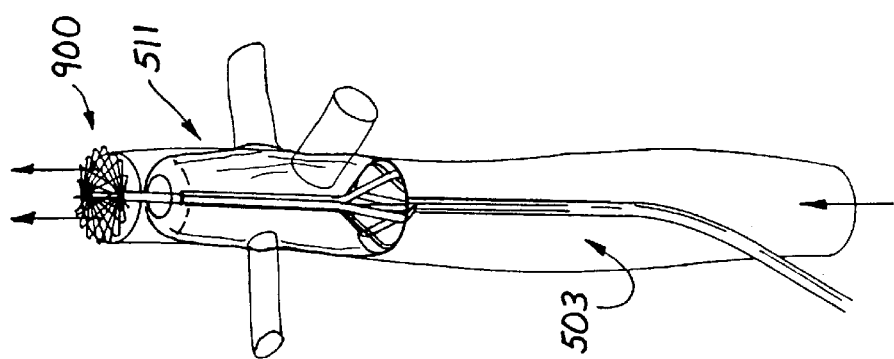
FIG. 36 is a perspective view illustrating the snare and the flow isolator deployed to a high-profile state in the primary body conduit.
Figure 35:
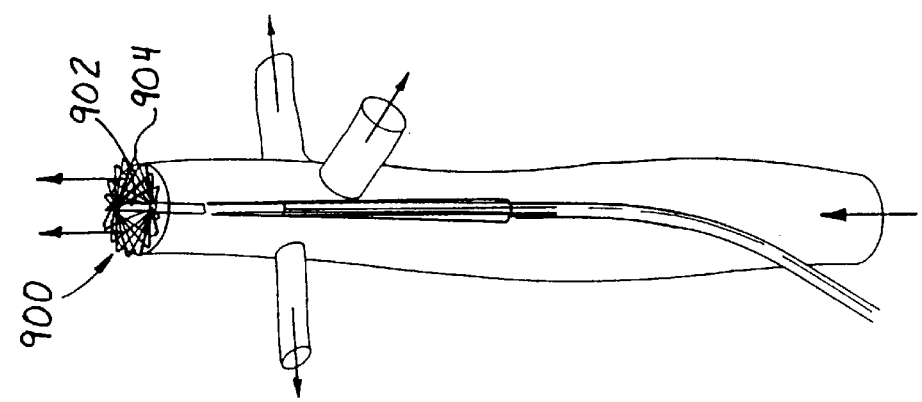
FIG. 35 is a perspective view of a FIG. 30 embodiment illustrating the snare deployed to a high-profile state.
Figure 34:
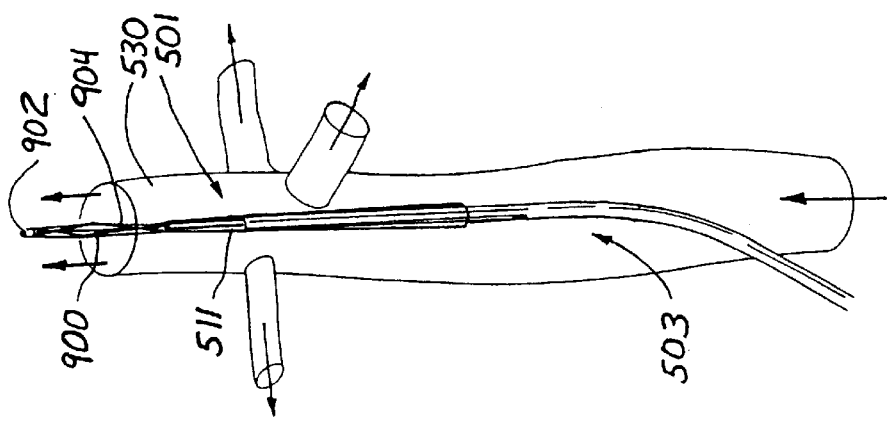
FIG. 34 is a perspective view of still a further embodiment of the invention, including a distal snare disposed in the primary body conduit in a low-profile state.

Any of the foregoing embodiments of the isolator 501 can be combined with a blood filter or a snare 900 preferably disposed distally as the isolator 501, as illustrated in FIGS. 34–36. Realizing that the placement of any foreign object into a vascular conduit, such as the inferior vena cava 530, may tend to generate blood clots, the snare 900 functions to inhibit flow of those clots beyond the distal end of the catheter 503. Thus, in the embodiment illustrated in FIG. 34, the catheter 503 is not only provided with the shaft 505 having the outer tube 507 and inner tube 510, but also further provided with an axial shaft 902 which extends to the distal end of the catheter 503. This axial shaft 902 is not only disposed within the inner tube 210, but also axially moveable relative to the inner tube 210.

The snare 900 can be formed of multiple filaments 904 connected between the distal end of the axial shaft 902 and the distal end of the inner tube 510. Movement of the shaft 902 within the tube 510 moves the filaments 904 and the snare 900 from a low-profile state illustrated in FIG. 34 to a high-profile state illustrated in FIG. 35. It will be noted that this deployment of the snare 900 is accomplished independently of the deployment of the flow isolator 501 in this embodiment. In a preferred method of operation, this deployment of the snare 900, as illustrated in FIG. 35, is accomplished before deployment of the flow isolator 501, as illustrated in FIG. 36. Any blood clots which may form as a result of the presence of the catheter 503 in the vena cava 530 will be caught by the filter or snare 900 which is disposed distally of the isolator 511.

Having described several embodiments of the invention which themselves differ in several respects, it will be apparent that the concept of this invention can be embodied in many different forms. For example, in the "wind sock" embodiment of FIG. 18, the fingers 525 can be replaced with many different mechanical and pneumatic structures well known in the art. Similar structures can be provided at the distal end of the isolator 511 to control the size of the outlet opening or hole 518 to further control pressurization of the sleeve 511. In the embodiment of FIG. 30, structures other than pneumatic chambers can be used to form the seals at the proximal and distal ends of the isolator 501. Similarly, the longitudinal chambers 804 which form the endoluminal shunt or sleeve 511 might be replaced by any structure providing a longitudinal force to separate the circumferential chambers 800 and 802. As long as this structure can form a continuous sleeve or barrier between the chambers 800 and 802, it will isolate the body fluid, such as blood, from the secondary conduits 532–538.

Due to the wide variations and improvements which can be made to these embodiments, one is cautioned not to limit the concept to the structural forms illustrated, but rather to determine the scope of the invention only with reference to the following claims.

What is claimed is:

1. A flow isolator adapted for use in controlling a flow of body fluid to a primary body conduit and to a secondary body conduit forming an intersection with the primary body conduit, the isolator including:
   a sleeve having a flexible wall with a proximal end and a distal end, the sleeve being adapted for operational disposition within the primary conduit and across the intersection with the secondary body conduit, with the distal end of the sleeve being adapted to face in the direction of flow of the body fluid in the primary body conduit;
   first portions of the sleeve at the proximal end of the sleeve being adapted to expand radially outwardly to form a seal with the primary body conduit proximally of the intersection with the secondary body conduit, to facilitate flow inwardly of the sleeve while inhibiting flow outwardly of the sleeve;
   intermediate portions of the sleeve between the proximal end and the distal end directing the flow of body fluid through the sleeve and past the intersection with the second body conduit; and
   second portions of the sleeve at the distal end of the sleeve directing the flow of body fluid from the sleeve into the primary body conduit distally of the intersection with the secondary body conduit.

2. The flow isolator recited in claim 1 wherein the second portions of the sleeve at the distal end of the sleeve are adapted to expand radially outwardly to form a second seal with the primary body conduit distally of the intersection with the secondary body conduit.

3. The flow isolator recited in claim 2 wherein the first portions of the sleeve form an inflatable circumferential chamber.

4. The flow isolator recited in claim 3 wherein the intermediate portions of the sleeve comprise at least one inflatable longitudinal chamber.

5. The flow isolator recited in claim 4 wherein the second portions of the sleeve form an inflatable circumferential chamber.

6. A flow isolator adapted for use in controlling a flow of a body fluid to a primary body conduit and to a secondary body conduit forming an intersection with the primary body conduit, the isolator including:

a sleeve having a flexible wall with a proximal end and a distal end, the sleeve being adapted for operational disposition within the primary conduit and across the intersection with the secondary body conduit, and with the distal end of the sleeve being adapted to face in the direction of flow of the body fluid in the primary body conduit;

first portions of the sleeve at the proximal end of the sleeve forming a first opening in the wall to facilitate flow of the body fluid into the sleeve;

second portions of the sleeve at the distal end of the sleeve forming a second opening in the wall to facilitate flow of the body fluid from the sleeve;

the second opening at the distal end of the sleeve being smaller than the first opening at the proximal end of the sleeve to increase the pressure of the body fluid within the sleeve;

the flexible wall of the sleeve being responsive to the increased pressure of the body fluid within the sleeve to move the wall against the primary conduit and thereby facilitate the flow of body fluid through the sleeve;

the sleeve in proximity to the primary conduit tending to block the intersection with the secondary body conduit to inhibit flow of the body fluid between the primary conduit and the secondary conduit;

an expansion structure disposed at the proximal end of the sleeve and being moveable from a low-profile state to a high-profile state;

the expansion structure having properties for moving the first portions of the sleeve to compress the first opening in the low-profile state in order to facilitate introduction of the sleeve, and to expand the first opening in the high-profile state in order to facilitate the flow of body fluid into the sleeve;

a plurality of fingers each contacting the sleeve at the first portions of the sleeve, the fingers being spaced from each other to facilitate flow of the body fluid through the first opening and into the sleeve; and the fingers being moveable between the low-profile state and the high-profile state.

7. A flow isolator adapted for use in controlling a flow of a body fluid to a primary body conduit and to a secondary body conduit forming an intersection with the primary body conduit, the isolator including:

a sleeve having a flexible lateral wall with a proximal end and a distal end, the sleeve being adapted for operational disposition within the primary conduit and across the intersection with the secondary body conduit, and with the distal end of the sleeve being adapted to face in the direction of flow of the body fluid in the primary body conduit;

first portions of the sleeve at the proximal end of the sleeve forming a first opening in the wall to facilitate flow of the body fluid into the sleeve;

second portions of the sleeve at the distal end of the sleeve forming a second opening in the wall to facilitate flow of the body fluid from the sleeve;

the second opening at the distal end of the sleeve being smaller than the first opening at the proximal end of the sleeve to increase the pressure of the body fluid within the sleeve;

the flexible wall of the sleeve being responsive to the increased pressure of the body fluid within the sleeve to move the wall against the primary conduit and thereby facilitate the flow of body fluid through the sleeve;

the sleeve in proximity to the primary conduit tending to block the intersection with the secondary body conduit to inhibit flow of the body fluid between the primary conduit and the secondary conduit;

an end wall disposed at the distal end of the sleeve and extending generally radially inwardly of the lateral wall to define the second opening at the distal end of the sleeve as a plurality of holes in the end wall of the sleeve.

8. The flow isolator recited in claim 7 wherein at least one of the plurality of holes has a configuration of an ellipse.

9. A flow isolator adapted for use in controlling a flow of a body fluid to a primary body conduit and to a secondary body conduit forming an intersection with the primary body conduit, the isolator including:

a sleeve having a flexible wall with a proximal end and a distal end, the sleeve being adapted for operational disposition within the primary conduit and across the intersection with the secondary body conduit, and with the distal end of the sleeve being adapted to face in the direction of flow of the body fluid in the primary body conduit;

first portions of the sleeve at the proximal end of the sleeve forming a first opening in the wall to facilitate flow of the body fluid into the sleeve;

second portions of the sleeve at the distal end of the sleeve forming a second opening in the wall to facilitate flow of the body fluid from the sleeve;

the second opening at the distal end of the sleeve being smaller than the first opening at the proximal end of the sleeve to increase the pressure of the body fluid within the sleeve;

the flexible wall of the sleeve being responsive to the increased pressure of the body fluid within the sleeve to move the wall against the primary conduit and thereby facilitate the flow of body fluid through the sleeve;

the sleeve in proximity to the primary conduit tending to block the intersection with the secondary body conduit to inhibit flow of the body fluid between the primary conduit and the secondary conduit; and the wall of the sleeve comprising a plurality of inflatable chambers disposed longitudinally of the sleeve.

10. A flow isolator adapted for use in controlling a flow of a body fluid to a primary body conduit and to a secondary body conduit forming an intersection with the primary body conduit, the isolator including:

a sleeve having a flexible wall with a proximal end and a distal end, the sleeve being adapted for operational disposition within the primary conduit and across the intersection with the secondary body conduit, and with the distal end of the sleeve being adapted to face in the direction of flow of the body fluid in the primary body conduit;

first portions of the sleeve at the proximal end of the sleeve forming a first opening in the wall to facilitate flow of the body fluid into the sleeve;

second portions of the sleeve at the distal end of the sleeve forming a second opening in the wall to facilitate flow of the body fluid from the sleeve;

the second opening at the distal end of the sleeve being smaller than the first opening at the proximal end of the sleeve to increase the pressure of the body fluid within the sleeve;

the flexible wall of the sleeve being responsive to the increased pressure of the body fluid within the sleeve to move the wall against the primary conduit and thereby facilitate the flow of body fluid through the sleeve;

the sleeve in proximity to the primary conduit tending to block the intersection with the secondary body conduit to inhibit flow of the body fluid between the primary conduit and the secondary conduit; and third portions of the wall defining a third opening at the intersection of the primary conduit and the secondary conduit, the third portions being moveable between a first position wherein the third opening facilitates communication of the body fluid between the primary conduit and the secondary conduit, and a second position wherein the third opening inhibits communication of the body fluid between the primary conduit and the secondary conduit.

11. A catheter adapted for introduction into a primary conduit and relative to a secondary conduit forming an intersection with the primary conduit, the catheter comprising:

a flow isolator having a high-profile state and a low-profile state, an obturator coupled to the flow isolator for introducing the flow isolator to an operative site in the primary conduit;

a braided tubular structure included in the flow isolator, the tubular structure being naturally expandable to the high-profile state and being longitudinally expandable to the low-profile state;

a balloon included in the flow isolator and disposed in juxtaposition to the tubular structure outside the tubular structure, the balloon being deflatable to the low-profile state and inflatable to the high-profile state; and the flow isolator in the low-profile state being adapted for introduction into the primary conduit, and in the high-profile state, being adapted to facilitate flow through the primary conduit while blocking the intersection to inhibit flow in the secondary conduit.

12. The catheter recited in claim 11 wherein the balloon of the flow isolator is disposed circumferentially of the braided tubular structure.

13. The catheter recited in claim 12 wherein the braided tubular structure coaxial with the balloon.

14. The catheter recited in claim 11 wherein the tubular structure is formed from a multiplicity of filaments interwoven to define a central channel through the tubular structure and a multiplicity of interstices providing fluid communication between the central lumen and regions disposed laterally of the tubular structure.

15. A method for controlling flow of a body fluid in a primary conduit and a secondary conduit forming an intersection with the primary conduit, comprising the steps of:

positioning across the intersection a flow isolator having a proximal end and a distal end, the distal end facing in the direction of normal flow of the body fluid within the primary conduit; and pressurizing the sleeve to force the sleeve against the primary conduit thereby facilitating flow of the body fluid in the primary conduit while inhibiting flow of the body fluid through the intersection between the primary conduit and the secondary conduit.

16. The method recited in claim 15 wherein the normal flow of body fluid in the primary conduit is in a particular direction, and the method further comprises the steps of:

during the positioning step placing the distal end of the flow isolator in the particular direction relative to the intersection of the primary conduit and the secondary conduit.

17. The method recited in claim 16 wherein the pressuring step includes the steps of:

providing the proximal end of the flow isolator with a first opening;

providing the distal end of the flow isolator with the second opening; and the second opening being smaller than the first opening to increase the pressure of the body fluid within the flow isolator.

18. The method recited in claim 15 further comprising the steps of:

providing the flow isolator with a plurality of chambers; and inflating the chambers during the positioning step to force the flow isolator against the primary conduit.

19. The method recited in claim 18 wherein the providing step includes the step of forming one of the chambers with a longitudinal configuration.

20. The method recited in claim 18 wherein the providing step includes the step of forming one of the chambers with a circumferential configuration.

21. The method recited in claim 18 wherein the inflating step includes the step of inflating the chambers with a gas.

22. The method recited in claim 18 wherein the providing step includes the step of:

forming the sleeve with at least one of the chambers disposed at the proximal end of the sleeve.

* * * * *